United States Patent [19]

Nestor et al.

[11] Patent Number: 6,083,953

[45] Date of Patent: Jul. 4, 2000

[54] 2- (2-AMINO-1,6-DIHYDRO-6-OXO-PURIN-9-YL) METHOXY-1,3- PROPANEDIOL DERIVATIVE

[75] Inventors: John Joseph Nestor, Cupertino; Scott William Womble, Fremont; Hans Maag, Menlo Park, all of Calif.

[73] Assignee: Syntex (U.S.A.) Inc., Palo Alto, Calif.

[21] Appl. No.: 08/812,991

[22] Filed: Mar. 4, 1997

Related U.S. Application Data

[63] Continuation of application No. 08/453,223, May 30, 1995, abandoned, which is a continuation-in-part of application No. 08/281,893, Jul. 28, 1994, abandoned.

[51] Int. Cl.⁷ .......................... A61K 31/52; C07D 473/18
[52] U.S. Cl. ............................. 514/262; 544/276
[58] Field of Search ............................. 514/262; 544/276

[56] References Cited

U.S. PATENT DOCUMENTS

| | | | |
|---|---|---|---|
| 4,355,032 | 10/1982 | Verheyden et al. | 424/253 |
| 5,043,339 | 8/1991 | Beauchamp | 514/274 |

FOREIGN PATENT DOCUMENTS

| | | |
|---|---|---|
| 0 158 847 | 10/1985 | European Pat. Off. |
| 0 187 297 | 7/1986 | European Pat. Off. |
| 0 249 248 | 12/1987 | European Pat. Off. |
| 0 308 065 | 3/1989 | European Pat. Off. |
| 0 375 329 | 6/1990 | European Pat. Off. |
| 1 523 865 | 6/1978 | United Kingdom. |
| 2 104 070 | 3/1983 | United Kingdom. |
| 2 122 618 | 1/1984 | United Kingdom. |
| 8829571 | 6/1990 | United Kingdom. |
| WO94/29311 | 12/1994 | WIPO. |

OTHER PUBLICATIONS

E. Jensen et al., "Synthesis, enzymatic hydrolysis and physico-chemical properties ... ", *Acta Pharm. Nord.*, 3(4), 243–247 (1991).

J.C. Martin et al., "Synthesis and Antiviral Activity of Various Esters ... ", *J. Pharm. Sci.*, 76(2), 180–184 (1987).

P.C. Maudgal et al., "Topical Treatment of Experimental Herpes Simplex Keratouveitis ... ", *Arch. Ophthalmol.*, 102, 140–142 (1984).

L. Colla et al., "Synthesis and Antiviral Activity of Water-soluble Esters of Acyclovir ... ", *J. Med. Chem.*, 26, 602–604 (1983).

L.M. Beauchamp et al., "Amino acid ester prodrugs of acyclovir", *Antiviral Chemistry & Chemotherapy*, 3(3), 157–164 (1992).

*Primary Examiner*—Mark L. Berch
*Attorney, Agent, or Firm*—Heller Ehrman White & McAuliffe

[57] ABSTRACT

The L-monovaline ester derived from 2-(2-amino-1,6-dihydro-6-oxo-purin-9-yl)methoxy-1,3-propanediol and its pharmaceutically acceptable salts are of value as antiviral agents with improved absorption.

6 Claims, No Drawings

2-(2-AMINO-1,6-DIHYDRO-6-OXO-PURIN-9-YL) METHOXY-1,3-PROPANEDIOL DERIVATIVE

CROSS-REFERENCE TO RELATED APPLICATIONS

This application is a continuation of app. Ser. No. 08/453,223, abandoned filed May 30, 1995; which is in turn a continuation-in-part of app. Ser. No. 08/281,893, filed Jul. 28, 1994, now abandoned.

BACKGROUND OF THE INVENTION

1. Field of the Invention

The present invention relates to a novel antiviral drug, particularly an amino acid ester of a purine derivative, and most particularly to an ester derived from ganciclovir and L-valine and pharmaceutically acceptable salts thereof. The invention also relates to intermediate compounds, synthetic methods for making the antiviral drug, and to methods of antiviral and related disease treatment, and pharmaceutical compositions therefor.

More specifically, the invention relates to the L-monovaline ester derived from 2-(2-amino-1,6-dihydro-6-oxo-purin-9-yl)methoxy-1,3-propanediol and its pharmaceutically acceptable salts.

2. Background Information

British Patent 1523865 describes antiviral purine derivatives with an acyclic chain in the 9-position. Among those derivatives 2-(2-amino-1,6-dihydro-6-oxo-1,6-dihydro-purin-9-yl)methoxy-ethanol with the INN name acyclovir has been found to have good activity against herpes viruses such as herpes simplex. While acyclovir has been found to be very effective upon topical or parenteral administration, it is only moderately absorbed upon oral administration.

U.S. Pat. No. 4,355,032 discloses the compound 9-[(2-hydroxy-1-hydroxymethyl-ethoxy)methyl]-guanine or 2-(2-amino-1,6-dihydro-6-oxo-purin-9-yl)methoxy-1,3-propanediol with the INN name ganciclovir. Ganciclovir is highly efficacious against viruses of the herpes family, for example, against herpes simplex and cytomegalovirus. It has a relatively low rate of absorption when administered orally and must be used at high dosages when administered by that route. Ganciclovir is most commonly administered via intravenous infusion. This mode of administration has the disadvantage of being very inconvenient to the patient, often requiring the services of a doctor, nurse or other health care professional. There is also a certain risk of infection which is particularly problematic for immunocompromised patients who receive treatment with ganciclovir and may have little resistance against infections. Therefore it has been highly desirable to provide ganciclovir with an improved oral absorption profile.

British Patent Application GB 2 122 618 discloses derivatives of 9-(2-hydroxyethoxymethyl)guanine of the generic formula

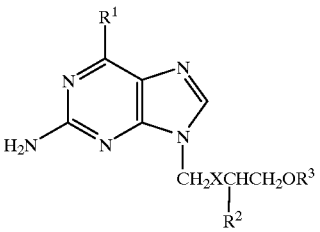

wherein X represents an oxygen or sulphur atom, $R^1$ represents a hydroxy or an amino group, $R^2$ represents a hydrogen atom or a group of the formula —$CH_2OR^3_a$ and $R^3$ and $R^3_a$ may be the same or different, each represents an amino acid acyl radical and physiologically acceptable salts thereof. These compounds are useful for the treatment of viral infections and have high water solubility which renders them of value in the formulation of aqueous pharmaceutical preparations. While the generic formula in the British patent application includes compounds in which $R^2$ is the group —$CH_2OR^3_a$, specific compounds of this group are not disclosed. The patent application also discloses that formulations used with these compounds with improved water-solubility include oral, rectal, nasal, topical, vaginal or parenteral formulations.

British Patent Application GB 2 104 070 A discloses antiviral compounds of the formula

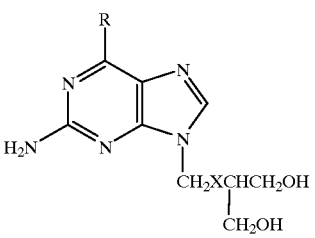

wherein R is a hydroxy or amino group and X is an oxygen or sulphur atom and physiologically acceptable salts and esters. The general formula includes ganciclovir and physiologically acceptable salts and esters. The esters include those containing a formyloxy group, $C_{1-16}$ (for example, $C_{1-6}$) alkanoyloxy (e.g. acetoxy or propionyloxy), optionally substituted aralkanoyloxy (e.g. phenyl-$C_{1-4}$ alkanoyloxy such as phenylacetoxy) or optionally substituted aroyloxy (e.g. benzoyloxy or naphthoyloxy) ester grouping at one or both of the terminal positions of the 9-side chain of the compounds of the general formula. The above-mentioned aralkanoyloxy or aroyloxy ester groups may be substituted, for example by one or more halogen (e.g. chlorine or bromo atoms) or amino, nitrile or sulphamido groups, the aryl moiety of the grouping advantageously containing 6 to 10 carbon atoms.

European Patent Application EP 0 375 329 discloses prodrug compounds with the following formula

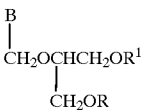

wherein R and $R^1$ are independently selected from a hydrogen atom and an amino acyl residue providing at least one of R and R¹ represents an amino acid acyl residue and B represents a group of the formulae

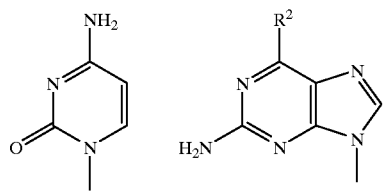

in which $R^2$ represents a $C_{1-6}$ straight chain, $C_{3-6}$ branched chain or $C_{3-6}$ cyclic alkoxy group, or a hydroxy or amino group or a hydrogen atom and the physiologically acceptable salts thereof. These prodrug compounds are described as having advantageous bioavailability when administered the oral route, resulting in high levels of the parent compound in the body.

Example 3b) European Patent Application EP 0 375 329 discloses the preparation of the bis(L-isoleucinate) ester of ganciclovir as white foam. Example 4b) discloses the preparation of the bis(glycinate) ester of ganciclovir as a white solid. Example 5b) discloses the preparation of the bis (L-valinate) ester of ganciclovir as a solid. Example 6b) discloses the preparation of the bis(L-alaninate) ester of ganciclovir as a syrup containing 90% of the bis ester and 10% of the monoester. The described bis esters are non-crystalline materials which are difficult to process for the manufacture of oral pharmaceutical dosage forms.

British Patent Application No. 8829571 discloses amino acid esters of the compounds of the formula

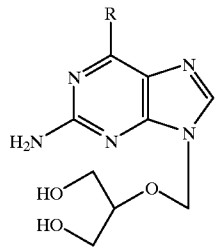

(wherein R represents a hydroxy or amino group or a hydrogen atom) and the physiologically acceptable salts thereof. Examples of preferred amino acids include aliphatic acids e.g. containing up to 6 carbon atoms such as glycine, alanine, valine and isoleucine. The amino acid esters include both, mono and diesters. However, this patent application as well as European Patent Publication 375 329 and U.S. Pat. No. 5,043,339 do not disclose the preparation of monoesters, much less any data suggesting their usefulness.

E. Jensen et. al., *Acta Pharm. Nord.* 3(4) 243–247 (1991) disclose the synthesis, enzymatic hydrolysis and physicochemical properties of N-substituted 4-(aminomethyl) benzoate diester prodrugs of ganciclovir of the formula

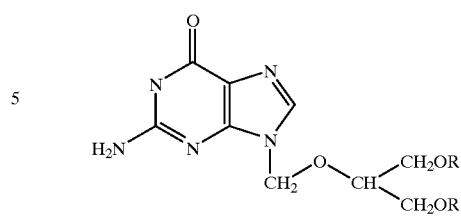

wherein R can be

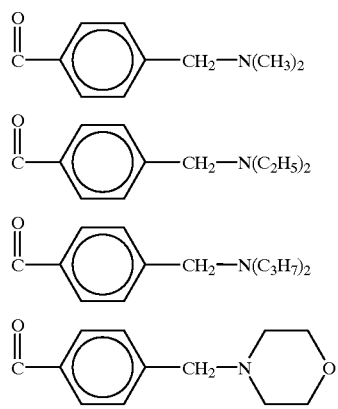

These esters were synthesized and evaluated with the aim of improving the delivery characteristics of ganciclovir. The esters were hydrolyzed enzymatically by human plasma to the parent drug, the hydrolysis proceeding through formation of the corresponding monoester. The authors evaluated these esters in terms of their rate of enzymatic hydrolysis, lipophilicity and concluded that the properties of these esters make the diesters a promising prodrug type for ganciclovir to enhance its delivery characteristics for e.g. parenteral administration.

John C. Martin et. al., *J. Pharm. Sci.* 76(2), p.180–184 disclose mono- and diacyl esters of ganciclovir which were tested to examine their bioavailability after oral administration. The authors indicate that the dipropionate ester is about 42% more bioavailable than ganciclovir itself.

European Patent Application 0 158 847 discloses inter alia that 6-deoxy-acyclovir and 6-deoxy-ganciclovir can be readily converted in vivo by the action of enzymes into acyclovir and ganciclovir, respectively. From experiments in rats the inventors found that oral administration of these 6-deoxy prodrugs results in efficient absorption from the gastro-intestinal tract and high plasma levels of the parent drugs.

P. C. Maudgal et. al., *Arch. Ophthalmol.* 1984; 102: 140–142 disclose the glycine ester of acyclovir as efficacious in the topical treatment of epithelial and stromal herpes simplex keratitis and associated iritis when administered as a 1% eye drop formulation to rabbits. The authors disclose the glycine, alanine, β-alanine and succinyl esters of acyclovir and indicate that the solubility of the glycine ester is about 30-fold greater than the solubility of acyclovir itself, which permits the use of the glycine ester for eye drops with concentrations up to 6%, while acyclovir itself is used as ointment which is hardly effective in stromal disease or iritis.

Leon Colla et. al., *J. Med. Chem.* 98, 3, 26, 602–604 disclose several water-soluble ester derivatives of acyclovir and their salts as prodrugs of acyclovir. The authors indicate that acyclovir cannot be given as eye drops or intramuscular injections because of its limited solubility in water and have therefore synthesized derivatives of acyclovir which are more water soluble than the parent compound. The authors disclose the hydrochloride salt of the glycyl ester, the hydrochloride salt of the alanyl ester, the hydrochloride salt of the β-alanyl ester, the sodium salt of the succinyl ester, and the azidoacetate ester. When assayed in primary rabbit kidney cell cultures against various herpes simplex virus type 1 and type 2 strains, according to the authors, the first four esters proved almost as active as acyclovir itself. The authors suggest that these acyclovir esters should be more practical for clinical use than the parent compound for topical treatment as eye drops and for systemic treatment of herpes virus infections that respond well to intravenous acyclovir treatment. In contrast with acyclovir, these esters could be given in much smaller volumes, and therefore via intramuscular injections.

L. M. Beauchamp et. al., *Antiviral Chemistry & Chemotherapy* (1992), 3 (3), 157–164 disclose eighteen amino acid esters of the antiherpetic drug acyclovir and their efficiencies as prodrugs of acyclovir, evaluated in rats by measuring the urinary recovery of acyclovir. Ten prodrugs produced greater amounts of the parent drug in the urine than acyclovir itself: the glycyl, D,L-alanyl, L-alanyl, L-2-aminobutyrate, D,L-valyl, L-valyl, DL-isoleucyl, L-isoleucyl, L-methionyl, and L-prolyl ester. The L-amino acid esters were better prodrugs than the corresponding D- or D,L-isomers, suggesting the involvement of a stereoselective transporter. From Table 1 of the publication which provides chemical data and oral bioavailability of the eighteen amino acid esters it follows that the D-amino acid esters have a lower oral bioavailability than acyclovir itself. Therefore, because the D-amino acid esters have no benefit over acyclovir they are not useful as prodrugs of acyclovir. The achiral glycyl ester of acyclovir, however, has a higher oral bioavailability than acyclovir (in the urinary recovery assay 30% of the acyclovir dosed as glycyl ester was recovered, whereas with acyclovir dosing 19% of the acyclovir was recovered). According to the authors the L-valyl ester of acyclovir was the best prodrug of the esters investigated.

European Patent Publication 308 065 discloses the valine and isoleucine esters of acyclovir, preferably in the L-form, as showing a large increase in absorption from the gut after oral administration, when compared with other esters and acyclovir.

Currently the leading drug for the treatment of cytomegalovirus infection is ganciclovir. However, its very limited oral bioavailability and the need for slow daily intravenous infusion of the drug (or for intravitreal injections or implants) indicate the urgent need for an oral dosage form with improved bioavailability.

The present invention provides a stable prodrug formulation of ganciclovir with improved oral absorption and low toxicity. Such characteristics are especially valuable for suppression of herpetic infections in immunocompromised patients where oral administration therapeutically is the preferred choice. In addition, the active ingredients exhibit pharmacopoeial properties which permit their improved characterization and pharmaceutical processing. Surprisingly, it was found that the L-monovaline ester of ganciclovir and its pharmaceutically acceptable salts exhibit these desired characteristics.

SUMMARY OF THE INVENTION

In a first aspect, this invention provides the compound of the formula I:

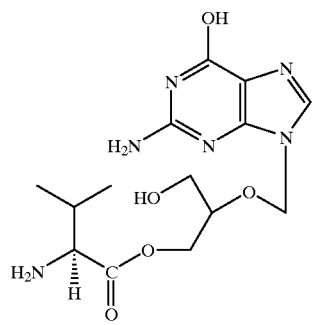

and pharmaceutically acceptable salts thereof. The compound is named hereinafter 2-(2-amino-1,6-dihydro-6-oxo-purin-9-yl)methoxy-3-hydroxy-1-propanyl-L-valinate or mono-L-valine ganciclovir.

In a second aspect, this invention provides a pharmaceutical composition which contains the mono-L-valine ester of ganciclovir or a pharmaceutically acceptable salt or diastereomer thereof, preferably in admixture with one or more suitable excipients or carriers.

In a third aspect, this invention provides a method of treating or preventing viral infections or related diseases comprising the administration of the mono-L-valine ester of ganciclovir or a pharmaceutically acceptable salt thereof or a composition containing same to an animal in need of such treatment or prevention.

In a fourth aspect, this invention provides compounds of Formula II which are useful intermediates for preparing mono-L-valine ganciclovir and its pharmaceutically acceptable salts:

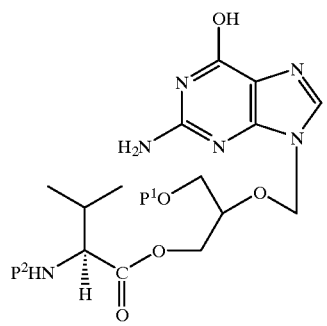

wherein $P_1$ is a hydroxy-protecting group and $P_2$ is an amino-protecting group.

A fifth aspect of this invention is a process for preparing the prodrug compound of the invention and its pharmaceutically acceptable salts. This process involves the esterification of ganciclovir and its derivatives, the removal of protecting groups from ganciclovir bis L-valine ester to the mono-L-valine ester of Formula I, the condensation of guanine with a substituted glycerol, the optical resolution of a compound of the Formula I, and the formation of salts of the prodrug of Formula I. Details of the process are described below.

DETAILED DESCRIPTION OF THE INVENTION

Definitions

Unless otherwise stated, the following terms used in the specification and claims have the meanings given below:

"Alkyl" means a straight or branched saturated hydrocarbon radical having from one to the number of carbon atoms designated. For example, $C_{1-7}$ alkyl is alkyl having at least one but no more than seven carbon atoms, e.g. methyl, ethyl, i-propyl, n-propyl, n-butyl,n-pentyl, n-heptyl and the like.

"Lower alkyl" means an alkyl of one to six carbon atoms.

"Aryl" means an organic radical derived from an aromatic hydrocarbon by the removal of one hydrogen atom. Preferred aryl radicals have six to twelve carbon atoms as ring carbon atoms in the aromatic hydrocarbon.

"Aralkyl" means an organic radical derived from an aralkane in which an alkyl hydrogen atom is substituted by an above-defined aryl group.

"Acyl" means an organic radical derived from an organic acid by the removal of the hydroxyl group; e.g., $CH_3CO-$ is the acyl radical of $CH_3COOH$, or acetyl. Other examples for such acyl groups are propionyl, or benzoyl, etc. The term "acyl" includes the term "alkanoyl" which is the organic radical RCO— in which R is an alkyl group as defined above.

"Lower alkoxy", "(lower alkyl)amino", "di(lower alkyl)amino", "(lower alkanoyl)amino", and similar terms mean alkoxy, alkylamino, dialkylamino, alkanoylamino, etc. in which the or each alkyl radical is a "lower alkyl" as described above.

"Halogen" means fluorine, chlorine, bromine, or iodine.

According to Hackh's *Chemical Dictionary*, McGraw-Hill Book Company, 1969, "derivative" of a compound means a compound obtainable from the original compound by a simple chemical process.

"Activated derivative" of a compound means a reactive form of the original compound which renders the compound active in a desired chemical reaction, in which the original compound is only moderately reactive or non-reactive. Activation is achieved by formation of a derivative or a chemical grouping within the molecule with a higher free energy content than that of the original compound, which renders the activated form more susceptible to react with another reagent. In the context of the present invention activation of the carboxy group is of particular importance and corresponding activating agents or groupings which activate the carboxy group are described in more detail below. An example of an activated derivative of L-valine is the compound of Formula III

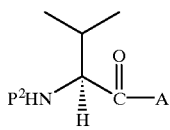

wherein $P^2$ is an amino-protecting group and A is a carboxy-activating group, for example, halo or a lower acyloxy group. A further example is an amino acid anhydride which is an activated form of an amino acid which renders the amino acid (especially L-valine) susceptible to esterification. Another example are UNCA's described in more detail below.

"Protecting group" means a chemical group that (a) preserves a reactive group from participating in an undesirable chemical reaction; and (b) can be easily removed after protection of the reactive group is no longer required. For example, the benzyl group is a protecting group for a primary hydroxyl function.

"Amino-protecting group" means a protecting group that preserves a reactive amino group that otherwise would be modified by certain chemical reactions. The definition includes the formyl group or lower alkanoyl groups with 2 to 4 carbon atoms, in particular the acetyl or propionyl group, the trityl or substituted trityl groups, such as the monomethoxytrityl group, dimethoxytrityl groups such as the 4,4'-dimethoxytrityl or 4,4'-dimethoxytriphenylmethyl group, the trifluoroacetyl, and the N-(9-fluorenylmethoxycarbonyl) or "FMOC" group, the allyloxycarbonyl group or other protecting groups derived from halocarbonates such as $(C_6-C_{12})$aryl lower alkyl carbonates (such as the N-benzyloxycarbonyl group derived from benzylchlorocarbonate), or derived from biphenylalkyl halo carbonates, or tertiary alkyl halo carbonates, such as tertiary-butylhalocarbonates, in particular tertiary butylchlorocarbonate, or di(lower)alkyldicarbonates, in particular di(t-butyl)-dicarbonate, and the phthalyl group.

"Hydroxy-protecting group" means a protecting group that preserves a hydroxy group that otherwise would be modified by certain chemical reactions. Suitable hydroxy-protecting groups include ether-forming groups that can be removed easily after completion of all other reaction steps, such as the benzyl or the trityl group optionally substituted in their phenyl ring. Other suitable hydroxy-protecting groups include alkyl ether groups, the tetrahydropyranyl, silyl, trialkylsilyl ether groups and the allyl group.

"Leaving group" means a labile group that is replaced in a chemical reaction by another group. Examples of leaving groups are halogen, the optionally substituted benzyloxy group, the isopropyloxy group, the mesyloxy group, the tosyloxy group or the acyloxy group.

All the activating and protecting agents employed in the preparation of the compound of Formula I must meet the following qualifications: (1) their introduction should proceed quantitatively and without racemization of the L-valine component; (2) the protecting group present during the desired reaction should be stable to the reaction conditions to be employed; and (3) the group must be readily removed under conditions in which the ester bond is stable and under which racemization of the L-valine component of the ester does not occur.

The term "chirality" means the property of handedness ascribed to a molecule which describes the symmetry elements of the molecule (or the absence of symmetry elements). Molecules that lack symmetry elements are "chiral". A chiral molecule lacking all of the symmetry elements, even including a simple axis, is termed "asymmetric".

The term "achiral" means the presence of at least one symmetry element in a molecule, such as a simple axis.

"Isomerism" refers to compounds having the same atomic mass and atomic number but differing in one or more physical or chemical properties. Various types of isomers include the following:

"Stereoisomer" refers to a chemical compound having the same molecular weight, chemical composition, and constitution as another, but with the atoms grouped differently. That is, certain identical chemical moieties are at different orientations in space and, therefore, when pure, have the ability to rotate the plane of polarized light. However, some pure stereoisomers may have an optical rotation that is so slight that it is undetectable with present instrumentation.

"Optical isomer" describes one type of stereo isomerism which manifests itself by the rotation that the isomer, either pure or in solution, imparts to the plane of polarized light. It is caused in many instances by the attachment of four different chemical atoms or groups to at least one of the carbon atoms in a molecule, or expressed alternatively, by the above-described chirality of the molecule.

Stereoisomers or optical isomers that are mirror images of one another are termed "enantiomers" and may be said to be enantiomeric. Chiral groups that are mirror images of one another are termed enantiomeric groups.

Enantiomers whose absolute configurations are not known may be differentiated as dextrorotatory (prefix+) or laevorotatory (prefix−) depending on the direction in which, under specified experimental conditions, they rotate the plane of polarized light.

When equal amounts of enantiomeric molecules are present together, the product is termed racemic, independently of whether it is crystalline, liquid, or gaseous. A homogeneous solid phase composed of equimolar amounts of enantiomeric molecules is termed a racemic compound. A mixture of equimolar amounts of enantiomeric molecules present as separate solid phases is termed a racemic mixture. Any homogeneous phase containing equimolar amounts of enantiomeric molecules is termed a racemate.

Compounds which have two asymmetric carbon atoms (chiral centers) have four stereoisomers which form two pairs of enantiomers. Whereas the enantiomers of a pair are mirror images of each other, the enantiomers of the two separate pairs are not mirror images of each other and are called "diastereomers". Diastereomers have similar but not identical chemical properties and have different physical properties, e.g. melting points, solubility, etc.

The optically active compounds herein can be designated by a number of conventions; i.e., the R- and S-sequencing rules of Cahn and Prelog; erythro and threo isomers; D and L-isomers; d and l-isomers; and (+) and (−) isomers, which indicates the direction a plane of polarized light is rotated by the chemical structure, either pure or in solution. These conventions are well known in the art and are described in detail by E. L. Eliel in *Stereochemistry of Carbon Compounds,* published by McGraw Hill Book Company, Inc. of New York in 1962 and references cited therein. Thus, these isomers may be described as d-, l- , or a d,l-pair; or D-, L-, or a D,L-pair; or R-, S-, or an R,S-pair; depending upon the nomenclature system employed. In general, this application will use the (D), (L) and (D,L) designation for the amino acid (valine), and the (R), (S) and (R,S) designation for the asymmetric carbon in the ganciclovir moiety to distinguish between the two.

The compound of Formula I and the compounds of Formula II have two asymmetric enters (2 carbon atoms), one in the valine component and the other in the aliphatic side chain of the ganciclovir component. The latter is the carbon atom 2 of the propanyl radical. Therefore the compound of Formula I and the compounds of Formula II exist as diastereomers and as mixtures of diastereomers. As concerns the compounds of the invention, any diastereomer or mixture of diastereomers may be used and the claims are intended to cover the individual diastereomers and mixtures thereof, unless otherwise restricted. Formula I includes the two diastereomers of Formula I, as well as mixtures thereof.

"Optional" or "optionally" means that a described event or circumstance may or may not occur, and that the description includes instances where said event or circumstance occurs and instances in which it does not. For example, "optionally substituted phenyl" means that the phenyl may or may not be substituted and that the description includes both unsubstituted phenyl and phenyl wherein there is substitution; "optionally followed by converting the free base to the acid addition salt" means that said conversion may or may not be carried out in order for the process described to fall within the invention, and the invention includes those processes wherein the free base is converted to the acid addition salt and those processes in which it is not.

"Pharmaceutically acceptable" means that which is useful in preparing a pharmaceutical composition that is generally safe and non-toxic and includes that which is acceptable for veterinary use as well as human pharmaceutical use.

"Pharmaceutically acceptable salts" means salts which possess the desired pharmacological activity and which are neither biologically nor otherwise undesirable. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxy-benzoyl)-benzoic acid, cinnamic acid, mandelic acid, methanesulfonic acid, ethanesulfonic acid, 1,2-ethanedisulfonic acid, 2-hydroxyethane-sulfonic acid, benzenesulfonic acid, p-chlorobenzenesulfonic acid, 2-naphthalenesulfonic acid, p-toluenesulfonic acid, camphorsulfonic acid, 4-methyl-bicyclo[2.2.2]oct-2-ene1-carboxylic acid, gluco-heptonic acid, 4,4'-methylenebis(3-hydroxy-2-naphthoic) acid, 3-phenylpropionic acid, trimethyl-acetic acid, tertiary butylacetic acid, lauryl sulfuric acid, gluconic acid, glutamic acid, hydroxy-naphthoic acids, salicylic acid, stearic acid, muconic acid, and the like. Preferred pharmaceutically acceptable salts are those formed with hydrochloric, sulfuric, phosphoric acid, acetic or methanesulfonic acid, ethanesulfonic acid, 1,2-ethanedisulfonic acid, 2-hydroxyethanesulfonic acid, benzenesulfonic acid, p-chlorobenzenesulfonic acid, and 2-naphthalenesulfonic acid, p-toluenesulfonic acid, camphorsulfonic acid.

Synthetic Reaction Parameters

Unless specified to the contrary, the reactions described herein take place at atmospheric pressure within a temperature range from 5° C. to 170° C. (preferably from 10° C. to 50° C.; most preferably at "room" or "ambient" temperature, e.g., 20–30° C.). However, there are clearly some reactions where the temperature range used in the chemical reaction will be above or below these temperature ranges. Further, unless otherwise specified, the reaction times and conditions are intended to be approximate, e.g., taking place at about atmospheric pressure within a temperature range of about 5° C. to about 100° C. (preferably from about 10° C. to about 50° C.; most preferably about 20° C.) over a period of about 1 to about 100 hours (preferably about 5 to 60 hours). Parameters given in the Examples are intended to be specific, not approximate.

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can, of course, also be used.

Medical Definitions

"Animal" includes humans, non-human mammals (such as dogs, cats, rabbits, cattle, horses, sheep, goats, swine, and deer) and non-mammals such as birds, fish and the like.

"Disease" specifically includes any unhealthy condition of an animal or part thereof. Thus, "disease" here includes any viral or related disease that is treatable with mono-L-valine ganciclovir or pharmaceutically acceptable salts thereof.

"Treatment" means any treatment of a disease in an animal and includes:

(1) preventing the disease from occurring in an animal which may be predisposed to the disease but does not yet experience or display symptoms of the disease; e.g., prevention of the outbreak of the clinical symptoms;

(2) inhibiting the disease, e.g., arresting its development; or (3) relieving the disease, e.g., causing regression of the symptoms of the disease.

"Effective amount" for the treatment of a disease means that amount which, when administered to an animal in need thereof, is sufficient to effect treatment, as defined above, for that disease.

Processes for Preparing Compounds of the Invention

The compound of Formula I or its pharmaceutically acceptable salts are prepared by a variety of methods. The synthetic approaches are apparent from the labelled dotted lines [(a) through (f)] in Formula I below. The dotted lines point schematically to the respective reaction sites and the ensuing table gives a brief description of the various methods that will be described in more detail below. The letter symbols in parentheses refer to the respective step in the process description/claim(s):

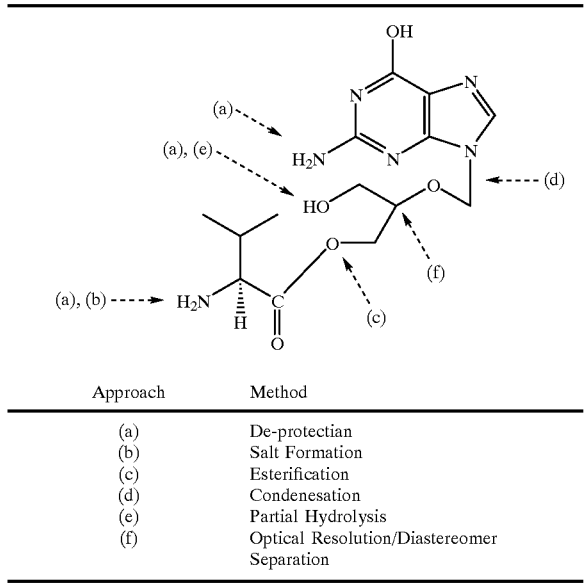

| Approach | Method |
|---|---|
| (a) | De-protectian |
| (b) | Salt Formation |
| (c) | Esterification |
| (d) | Condenesation |
| (e) | Partial Hydrolysis |
| (f) | Optical Resolution/Diastereomer Separation |

Accordingly, the process for the preparation of the compound of Formula I or a pharmaceutically acceptable salt thereof comprises one or more of the following steps:

(a) removal of an amino- and/or hydroxy-protecting group from a compound with the Formula IV

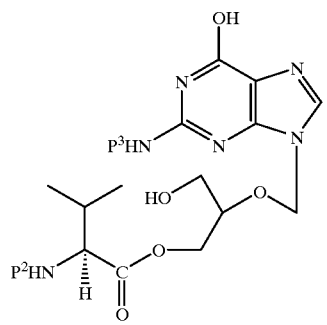

wherein $P^1$ is a hydroxy-protecting group or hydrogen, $P^2$ is an amino-protecting group, and $P^3$ is hydrogen or $P^2$ to afford the compound of Formula I;

(b) conversion of the compound of Formula I into a pharmaceutically acceptable salt thereof;

(c) esterification of 2-(2-amino-1,6-dihydro-6-oxo-purin-9-yl)methoxy-1,3-propanediol (ganciclovir) or a salt thereof, with an activated derivative of L-valine;

(d) condensation of an optionally substituted guanine of the Formula (V)

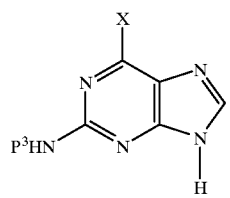

optionally in persilylated form,
wherein $P^3$ is hydrogen or an amino-protecting group, with a 2-substituted glycerol of the Formula (VI)

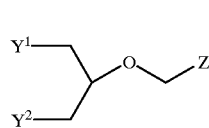

(V)

wherein $Y^1$ and $Y^2$ independently are halo, lower acyloxy, lower alkyloxy, or aralkyloxy groups, and Z is a leaving group selected from lower acyloxy, methoxy, isopropyloxy, benzyloxy, halo, mesyloxy or tosyloxy, and the like; optionally in the presence of a Lewis acid catalyst, to provide the compound of Formula I; or (e) partial hydrolysis of the bis ester 2-(2-amino-1,6-dihydro-6-oxo-purin-9-yl)methoxy-1,3-propanediyl bis (L-valinate) or a salt thereof to afford the monoester of the Formula I; or (f) optical resolution or diastereomeric separation of a compound of Formula (I).

Utility and Testing

The compound of Formula I and its pharmaceutically acceptable salts exhibit pharmaceutical activity and in particular antiviral activity. As such, the compound and its pharmaceutically acceptable salts are useful for treating a broad range of conditions in animals, particularly humans.

Examples of conditions that may be treated using the compound and salts of this invention include herpes infections such as herpes types 1, 2 and 6, varicella Zoster, Eppstein-Barr virus, and in particular cytomegalovirus, and hepatitis B and related viruses, in humans or non-human animals, particularly in humans. Examples of clinical conditions caused by these viruses are herpetic keratitis, herpetic encephalitis, cold sores, genital infections (caused by herpes simplex), chicken pox, shingles (caused by varicella Zoster), CMV-pneumonia and -retinitis, particularly in immunocompromised patients including transplant recipients (for example, heart, renal and bone marrow transplants) and patients with Acquired Immune Deficiency Syndrome (AIDS), Eppstein-Barr virus-caused infectious mononucleosis. The compound of the invention is also useful for the treatment of certain carcinomas or lymphomas caused by, or related to, viral infections, such as nasopharyngeal cancer, immunoblastic lymphoma, Burkitt's lymphoma, and hairy leukoplakia.

In summary, then another aspect of this invention is a method for treating an animal (preferably a human) exhibiting a condition in which an above-described viral infection plays a role, or prophylactically treating an animal where such viral infection is anticipated by the treating physician or veterinarian. The method comprises administering a therapeutically effective amount of mono-L-valine ganciclovir or its pharmaceutically acceptable salts to such animal. A therapeutically effective amount of the compound or its pharmaceutically acceptable salts is an amount that is efficacious in treating the condition, i.e. the disease. The exact amount administered may vary over a wide range depending on the degree of severity of the specific condition being treated, age and weight of the subject, relative health of the subject and other factors (such as type of formulation). For an oral formulation a therapeutically effective amount may vary from about 1 to 250 mg per Kg body weight per day, preferably about 7 to 100 mg/Kg body weight per day. Most preferably the therapeutically effective amount is about 10 to 50 mg/Kg/day, especially for the treatment of CMV retinitis and pneumonia. Thus, for a 70 Kg human, a therapeutically effective amount is from about 70 mg/day to about 7 g/day, preferably about 500 mg/day to about 5 g/day, most preferably 700 mg/day to 3.5 g/day. For an intravitreal implant, however, the does of the prodrug will range from 0.5 mg to 25 mg, preferably from 5 to 10 mg per implant. It is well understood by those skilled in the art that different dosage forms of the prodrugs of the invention will command different dosage ranges.

Ganciclovir is a proven antiviral drug. The utility of the ganciclovir prodrug of the present invention has been established by determining the blood level concentrations of ganciclovir in test animals (the rat and the monkey), following oral administration of the prodrug. The blood plasma level concentrations were determined according to the methods described in Examples 9 and 10 and are procedures which modified procedures described by Jean-Pierre Sommadossi et. al. in REVIEWS OF INFECTIOUS DISEASES, VOL. 10, SUPPLEMENT 3, p. S507 and in *Journal of Chromatography, Biomedical Applications,* 414 (1987), 429–433.

Administration and Pharmaceutical Composition

The compound or its pharmaceutically acceptable salts of this invention may be administered via any of the usual and acceptable modes known in the art, either singly or in combination with another therapeutic agent. Generally the compound and salts of this invention are administered as a pharmaceutical composition with a pharmaceutically acceptable excipient and are administered orally, systemically (e.g. transdermally, or by suppository) or parenterally (e.g. intramuscularly [im], intravenously [iv], subcutaneously [sc]) or intravitreally by an implant. The compound of the invention can thus be administered in a composition that is a semisolid, powder, aerosol, solution, suspension or other appropriate composition, as discussed hereinafter. Oral pharmaceutical compositions are preferred.

A pharmaceutical composition comprises the compound of Formula I or its pharmaceutically acceptable salts, preferably in combination with a pharmaceutically acceptable excipient. Such excipient is one that is non-toxic. Such excipient may be any solid, liquid, semisolid, gaseous (in case of an aerosol) excipient that is generally available to one of skill in the art and that does not adversely affect the activity of the active agent.

In general, the pharmaceutical composition of this invention will contain a therapeutically effective amount of the compound or its pharmaceutically acceptable salts in combination with at least one excipient. Depending on the type of formulation, size of a unit dosage, kind of excipients and other factors known to those of sill in the art of pharmaceutical sciences the amount of compound of this invention may vary over a wide range in the composition. In general, the final composition will comprise about 1% to about 99.5% wt of a compound of the invention with the remainder being the excipient or excipients. Preferably the level of active compound will be about 10.0% wt to about 99.% wt and most preferably about 50% wt to about 99% wt, with the remainder being a suitable excipient or excipients. Useful pharmaceutical excipients for the preparation of the pharmaceutical compositions hereof can be solids, semisolids, liquids or gases. Thus, the compositions can take the form of tablets, pills, capsules, powders, suppositories, transdermal patches, sustained release formulations, intravitreal implants, solutions, in particular intravenous solutions, suspensions, elixirs, aerosols, and the like. Solid pharmaceutical excipients include starches, such as corn starch, cellulose, talc, glucose, lactose, sucrose, gelatin, malt, rice, flour, chalk, silica gel, magnesium stearate, sodium stearate, stearic acid, glycerol monostearate, sodium chloride, dried skim milk, and the like. Liquid and semisolid excipients may be selected from water, ethanol, glycerol, propylene glycol, various oils, including those of petroleum, animal, vegetable or synthetic origin, for examples, peanut oil, soybean oil, mineral oil, sesame oil, and the like. Water, saline, aqueous dextrose, and glycols are preferred liquid carriers, particularly for injectable solutions. Other suitable pharmaceutical excipients and carriers and their formulations are described in *"Remington's Pharmaceutical Sciences"* by E. W. Martin, incorporated herein by reference.

Preferably the pharmaceutical composition is administered in a single unit dosage form, more preferably an oral dosage form, for continuous treatment or in a single unit dosage form ad libitum when relief of symptoms is specifically required.

Presently Preferred Embodiments

While the broadest definition of this invention is set forth in the Summary of the Invention as the compound of Formula I and its pharmaceutically acceptable salts, the (R,S) mixture and certain salts are preferred.

The following acids are preferred to form pharmaceutically acceptable salts with the compound of Formula I: hydrochloric, sulfuric, phosphoric acid, acetic, methanesulfonic, ethanesulfonic, 1,2-ethanedisulfonic, 2-hydroxyethanesulfonic, benzenesulfonic, p-chlorobenzenesulfonic, 2-naphthalenesulfonic, p-toluenesulfonic and camphorsulfonic acid. Most preferred are strong inorganic acids, such as hydrochloric, sulfuric or phosphoric acid.

The most preferred compounds are 2-(2-amino-1,6-dihydro-6-oxo-purin-9-yl)methoxy-3-hydroxy-1-propanyl L-valinate hydrochloride and acetate. These compounds can be prepared as crystalline materials and therefore can be easily manufactured into stable oral formulations. Oral and intravenous formulations are preferred. The oral formulations have the advantage of high bioavailability; the intravenous formulations have the advantage that the prodrug of the invention, unlike intravenous ganciclovir formulations be prepared using a physiologically more acceptable pH (4–6). The intravenous formulation of ganciclovir requires a pH of 11 which results in irritation.

It is understood that these compounds are particularly useful in the pharmaceutical compositions and methods of treatment of this invention.

In any of the last step processes described herein, a reference to Formula I, II, III, IV, V or VI refers to such Formulae wherein $P^1$, $P^2$, and $P^3$, A, $Y^1$, $Y^2$ and Z are as defined in their broadest definitions set forth in the Summary of the Invention, with the processes applying particularly to the presently preferred embodiments.

The preferred pharmaceutical compositions of this invention contain a pharmaceutically acceptable salt of the prodrug of Formula I. Accordingly, if the manufacture of pharmaceutical formulations involves intimate mixing of the pharmaceutical excipients and the active ingredient in its salt form, then it is preferred to use pharmaceutical excipients which are non-basic in nature, i.e., either acidic or neutral.

Details of the Synthetic Processes

The currently preferred process for producing the compound of the Formula I involves step (a), preferably carried out with the concomitant formation of a salt of a compound of Formula I, or step (c), or a combination of steps (a) and (c). (See the description of Steps III and IV below). The preparation of the monoester according to step (a) requires the selective protection of one of the two primary hydroxyl functions of ganciclovir or its derivative. This generally may or may not involve protection of the amino group in the 2-position of the guanine base (see the detailed description below of Steps I through III for the case the process is carried out with a protected amino group). In addition, before the esterification (Step III) is carried out, the amino group of the amino acid reagent must be protected, to avoid its interference (amide formation) in the esterification reaction. The protection of the amino group is described in the section "Preparation of the N-Protected Amino Acid" below.

In general, when carrying out a process of this invention, those amino, hydroxy or carboxylic groups which are not to participate in the synthesis reaction must be protected until (1) either de-protection yields the final product; or (2) a specific protected group is to be involved in the next synthetic step; or (3) the presence of the unprotected group in the ensuing reaction steps leading to the final product would not modify the intended sequence of reactions. An example for meeting requirement (1) is the benzyl group in the preparation of the monoesters of this invention, which protects one primary hydroxyl function of ganciclovir until it is removed in the de-protection step. An example for meeting requirement (2) is the second benzyl group protecting the second primary hydroxyl function of ganciclovir which is removed just prior to the esterification step. An example for meeting requirement (3) is the acetyl group, or the trityl or monomethoxytrityl group protecting the amino group of the guanine ring system of ganciclovir, as the unprotected amino group does not interfere with the esterification (step III).

In general, the qualification of potential blocking agents that render them suitable for use in the preparation of the compound of Formula I include:

(1) Their introduction should proceed quantitatively and smoothly without L-valine racemization;

(2) The blocked intermediate must be stable to conditions of the reactions employed until removal of the protecting group is required;

(3) The blocking group must be susceptible of being readily removed under conditions which do not change the chemical nature of the remainder of the molecule or result in racemization of the L-valine component.

Starting Materials

All starting materials (ganciclovir and L-valine) and the protecting and carboxylic-group-activating reagents employed to make the compound of Formula I are known. Also known are various amino-protected L-valine derivatives, such as N-benzyloxycarbonyl-L-valine, BOC-L-valine and FMOC-L-valine, N-formyl-L-valine and N-benzyloxycarbonyl-N-carboxy-L-valine anhydride, which are all commercially available intermediates, or described in the literature, such as N-allyloxycarbonyl-L-valine.

A preferred protected ganciclovir starting material for the preparation of the preferred compound of the invention is N2-acetyl-bis-O-benzyl-ganciclovir (N2-acetyl-2-(2-amino-1,6-dihydro-6-oxo-purin-9-yl)methoxy-1,3-bis(benzyloxy) propane) which is described in U.S. Pat. No. 4,355,032. Other preferred protected ganciclovir starting materials are $N^2$-trityl-9-[(3-hydroxy-2-propoxy-1-trityloxy)methyl] guanine [$N^2$-trityl-2-(2-amino-1,6-dihydro-6-oxo-purin-9-yl)methoxy-1-trityloxy-propan-3-ol] $N^2$-monomethoxytrityl-9-[(3-hydroxy-2-propoxy-1-monomethoxytrityloxy)methyl]- guanine, the preparation of which is described in *J. Pharm. Sci.* 76(2), p.180–184 (1987) which is incorporated herein by reference 2-(2-Amino-1,6-dihydro-6-oxo-purin-9-yl)methyl-1,3-propanediyl bis(L-valinate) which is the starting material for the partial hydrolysis step is described in European Patent publication 0 375 329.

Preparation of the N-Protected Amino Acid

Prior to carrying out Step III (esterification step), the amino group of L-valine must be protected to avoid its interference with the esterification by undersirable amide formation. The following amino-protecting groups are useful: halocarbonates such as ($C_6$–$C_{12}$) aryl lower alkyl carbonates (such as the carboboenzyloxy group derived from benzylchlorocarbonate), or biphenylalkyl halo carbonates, or tertiary alkyl halo carbonates, such as tertiary-butylhalocarbonates, in particular tertiary butylchlorocarbonate, or di(lower)alkyldicarbonates, in particular di(t-butyl)dicarbonate, triphenylmethyl halides such as triphenylmethyl chloride, and trifluoroacetic anhydride. The protecting step is carried out by dissolving or suspending L-valine in an alkaline aqueous solution which may include a lower alkanol. The reaction mixture is cooled while the protecting reagent such as the halocarbonate, preferably in an aqueous or lower alkanol solution is added simultaneously in small portions. During this addition, the reaction mixture is kept at 0 to 30°, preferably 0–5° C. for several hours until it reaches room temperature. The reaction mixture is concentrated to dryness and the residue is partitioned between an organic phase and water. The aqueous layer is acidified and extracted with an organic solvent for the protected amino acid. The organic phase is washed with water followed by brine washings and dried over magnesium sulfate before evaporation to dryness, and the N-protected amino acid isolated and purified by conventional isolation and purification techniques.

Preparation of Mono-L-valine Ganciclovir

Step I: Ganciclovir, with an optionally protected 2-amino group and both primary hydroxyl functions protected is partially de-protected, for example, by hydrogenation to ganciclovir with the 2-amino group retained in protected form and one protected primary hydroxyl function. Suitable amino-protecting groups are lower alkanoyl groups with 2 or 4 carbon atoms, in particular the acetyl or propionyl group. Other suitable amino-protecting groups are the trityl or substituted trityl groups, such as the monomethoxytrityl group, and the 4,4'-dimethoxytrityl group.

Suitable hydroxy-protecting groups are ether-forming groups that can be removed easily after completion of all other reaction steps. These hydroxy-protecting ether groups include the benzyl or the trityl group. These groups may be substituted in the phenyl ring. Other suitable hydroxy-protecting groups include allyl ether, tetrahydropranyl, silyl, trialkylsiyl ethers which can be removed with hydrogen fluoride in a manner known well to those skilled in the art.

The hydrogenation to remove one hydroxy-protecting group is preferably carried out by dissolving the protected ganciclovir in a solvent system that releases hydrogen in the presence of a catalyst such as a palladium compound, in particular palladium hydroxide, by transfer hydrogenation or other conventional hydrogenation procedures. Other suitable hydrogenation catalysts include hydrogenation catalysts in general such as Pd, Pd on carbon and homogeneous hydrogenation catalysts. The solvent system includes a lower alkanol such as methanol or ethanol and cyclohexane. Generally the reaction will be carried out at temperatures between room temperature and the reflux temperature of the solvent system, for example in refluxing ethanol and cyclohexane under an inert atmosphere and under exclusion of oxygen or air, preferably in a nitrogen atmosphere. The catalyst will be recovered by filtration. The filtrate can be reduced in volume by evaporation of excess solvent. The resulting crude reaction mixture generally includes unchanged starting material and 2-amino-protected ganciclovir and one aliphatic hydroxy group protected as the major products. The separation of these two products is usually performed by isolation procedures known in the art, often by chromatographic methods, preferably on silica gel, followed by elution with appropriate eluents such as mixtures of a lower alkanol with a halogenated lower alkane (preferably ethanol and dichloromethane) to give 2-amino-protected ganciclovir with one aliphatic hydroxy group protected.

Step II: Ganciclovir with a protected 2-amino group and one aliphatic hydroxy group protected is subjected to de-protection of the amino group. In this step if the amino-protecting group is a lower alkanoyl group basic conditions (pH between 9 to 14) are employed to remove the protecting group. For example, N2-Acetyl-mono-O-benzyl-ganciclovir is treated with an alkaline reagent such as ammonium hydroxide, sodium or potassium carbonate or sodium or potassium hydroxide until the removal of the acetyl group is complete. In general, this reaction will be conducted in the presence of a suitable solvent such as a lower alkanol. Preferably the starting material is dissolved in methanol and a stoichiometric excess of ammonium hydroxide is added. The reaction temperature is kept between 0 to 50° C., preferably at room temperature. After the reaction is complete (which can be determined by TLC), another solvent may be added to facilitate isolation of the de-protected product, such as ethyl ether which leads to precipitation of the de-acylated product which can be filtered off and isolated using conventional separation methods.

Step III: In this step an activated derivative of amino-protected L-valine of the Formula III is esterified with the protected ganciclovir derivative obtained in Step II. Suitable amino-protecting groups for L-valine are the N-benzyloxycarbonyl group, the phthalyl group, the tertiary butyloxycarbonyl group and the N-(9-fluorenylmethoxycarbonyl) or "FMOC" group.

At least 1 equivalent of the protected amino acid and 1 equivalent of a suitable coupling agent or dehydrating agent, for example 1,3-dicyclo-hexylcarbodiimide or salts of such diimides with basic groups should be employed from the start. Other carbodiimides such as N,N'-carbonyldiimidazole may also be used. Further useful dehydrating agents are trifluoroacetic anhydride, mixed anhydrides, acid chlorides, 1-benzo-triazolyloxy-tris(dimethylamino) phosphonium hexafluorophosphate, PYBOP, 1-hydroxybenzotriazole, 1-hydroxy-4-azabenzotriazole, 1-hydroxy-7-azabenzotriazole, N-ethyl-N'-ethyl-N-40-(3-(dimethylamino-propyl)carbodiimide hydrochloride, 3-hydroxy-3,4-dihydro-4-oxo-1,2,3-benzotriazine, O-(benzotriazol-1-yl)-1,1,3,3-tetramethyluronium hexafluorophosphate, O-(7-azabenzotriazol-1-yl)-1,1,3,3-tetramethyluronium hexafluorophosphate, O-(7-azabenzotriazol-1-yl)-1,1,3,3-tetramethyluronium tetrafluoroborate, O-(1H-benzotriazol-1-yl)-1,1,3,3-bis (tetramethylene)-uronium hexafluorophosphate or O-(7-azabenzotriazol-1-yl)-1,1,3,3-bis(tetramethylene)uronium hexafluorophosphate. A description of these coupling agents by L. A. Capino can be found in *J. Am. Chem. Soc.* 1993, 115, p. 4397–4398. Also useful for this purpose are urethane-protected amino acid N-carboxy anhydrides (UNCA's) which have been described by William D. Fuller et. al., *J. Am. Chem. Soc.* 1990, 112, 7414–7416, which is incorporated herein by reference. In summary, any other reagent that produces an anhydride or another activated derivative of the protected amino acid under mild conditions can be used as the coupling agent.

The amino-protected amino acid is dissolved in an inert solvent such as a halogenated lower alkane, preferably dichloromethane under an inert atmosphere, for example nitrogen, and the coupling agent is added (preferably 1,3-dicyclohexylcarbodiimide). The reaction mixture is stirred at temperature between 0 and 50° C., preferably at about room temperature. The reaction mixture is filtered and the reaction product (the anhydride of dry inert solvent such as dry DMF and placed under nitrogen. A solution of an equivalent amount of the product of Step II in an inert solvent is added to the above solution of the anhydride. The reaction is carried out between 0 and 50° C., preferably at about room temperature over 5 to 90 hours. The reaction product can be isolated and purified using conventional methods, such as chromatography. The product usually will contain unreacted N-protected amino acid which can be removed by treatment of a water-immiscible solution (organic phase) of the product with aqueous alkali such as sodium bicarbonate, sodium carbonate, brine and mixtures thereof. From the organic phase the ganciclovir L-valine ester with the protected aliphatic hydroxy group and the N-protected amino acid can be isolated and purified using conventional isolation and purification techniques.

Step IV (Final De-protection to Give the Product of Formula I): The two protecting groups of the product of Step III are removed by de-protection reactions, preferably in an acidic medium or solvent, most preferably by hydrogenation. De-protection under acidic conditions is preferred, as this will ensure that the amino group liberated in the de-protection reaction will be protonated, that is that the base of Formula I as it is formed in the de-protection reaction will be captured by an at least stoichiometric amount of acid present. Isolating the compound of Formula I as an acid addition salt will protect the desired stereoconfiguration of the compound of Formula I. Therefore, those examples given below that show the de-protection step (a) also show the concomitant salt formation step (b).

The de-protection reaction is carried by dissolving the product of the esterification step in an inert solvent, preferably in an acidic solvent, using an hydrogenation catalyst, such as palladium on carbon, platinum, using elevated hydrogen pressure between 1 and 2000 psi, preferably 20 to 200 psi. The completion of the reaction can be monitored using conventional TLC analysis. The hydrogenation is continued until the conversion is complete, if required with addition of further hydrogenation catalyst. The catalyst is removed and washed. The combined filtrates from filtration and the washings are concentrated and lyophilized to isolate ganciclovir L-valine ester. The purification of the product and the isolation of a crystalline ester is carried out by recrystallization or other purification techniques, such as liquid chromatographic techniques.

If the tertiary butyloxycarbonyl group is being used as amino-protecting group, its removal is effected with acid, such as HCl and isopropanol as a solvent or with trifluoroacetic acid neat.

Alternatively if the esterification step has been carried out with a trityl or substituted trityl-protected ganciclovir derivative such protecting groups can be removed by treatment with an aqueous alkanoic acid or trifluoroacetic or hydrochloric acid at temperature between −2020 C. and 100° C., for example aqueous acetic acid.

Allyl groups are removed by isomerization to the vinyl ethers with rhodium or palladium catalysts, followed by acidic aqueous hydrolysis.

Other Methods of Preparation [Steps (b), (d), and (e)]

One of ordinary skill in the art will also recognize that the compound of Formula I may be prepared as an acid addition salt or as the corresponding free base. If prepared as an acid addition salt, the compound can be converted to the free base by treatment with a suitable base such as ammonium hydroxide solution, sodium hydroxide, potassium hydroxide or the like. However, it is important to point out that the free base of Formula I is more difficult to characterize than its acid addition salts. When converting the free base to an acid addition salt, the compound is reacted with a suitable organic or inorganic acid (described earlier). These reactions are effected by treatment with an at least stoichiometric amount of an appropriate acid (in case of the preparation of an acid addition salt) or base (in case of liberation of the free compound of Formula I). In the salt-forming step of this invention typically, the free base is dissolved in a polar solvent such as water or a lower alkanol (preferably isopropanol) and mixtures thereof and the acid is added in the required amount in water or in lower alkanol. The reaction temperature is usually kept at about 0 to 50° C., preferably at about room temperature. The corresponding salt precipitates spontaneously or can be brought out of the solution by the addition of a less polar solvent, removal of the solvent by evaporation or in a vacuum, or by cooling the solution.

The reaction conditions of condensation step (d) are described in European Patent Publication 187 297. This condensation step is one of the preferred methods for the preparation of the diastereomers of the monoester. In this condensation step guanine, preferably with a protected 2-amino group is reacted with a glycerol derivative. The glycerol derivative, such as a 1-halo-3-benzyloxy-2-acyloxymethoxyglycerol, is reacted with guanine or a substituted guanine derivative in an aprotic hydrocarbon solvent (such as benzene or toluene, or xylenes) or DMF with a hexa-lower alkyl silazane, for example, hexamethylsilazane, hexaethylsilazane, or the like, and a catalyst at temperatures between 30° C. and reflux temperature. The catalyst is a Lewis acid salt, such as trialkyl silyl salt, such as the sulfate or a trifluoroalkyl sulfonate, a chlorosilane, or ammonium sulfate and pyridine. For a more detailed disclosure of the reaction conditions for condensation step (d) see the disclosure of European Patent Publication 187 297 which is incorporated by reference herein. In general, $Y^1$ and $Y^2$ need to be chosen in such a way as to permit the obtention of the mono-L-valine ester of Formula I. $Y^1$ can be an amino-protected L-valinyl group, or a group convertible to the L-valinyl group.

The compound of this invention may also be prepared from 2-(2-amino-1,6-dihydro-6-oxo-purin-9-yl)methoxy-1,3-propanediyl bis(L-valinate) which is described in European Patent publication 0 375 329. The conversion to 2-(2-amino-1,6-dihydro-6-oxo-purin-9yl)methyoxy-3-hydroxy-1-propanyl-L-valinate is effected by partial hydrolysis [Step (e)] of one L-valine ester group under controlled conditions which result in the preferential cleavage of only one amino acid acyl residue. A salt of 2-(2-amino-1,6-dihydro-6-oxo-9H-purin-9-yl)methoxy-1,3-propanediyl bis-L-valinate, preferably as the bis acetate salt, is dissolved in de-ionized water, and partially neutralized with weak base, such as a dilute ammonium hydroxide solution. The mixture will is kept at room temperature for one to several days, preferably 48 to 72 hrs.

Alternatively, enzymatic hydrolysis with an esterase, such as porcine esterase or a peptidase, such as a carboxypeptidase can also be used to effect partial hydrolysis.

The monoester can be separated from the bis ester by preparative chromatography under weak acidic conditions (pH 3 to 5, preferably pH 4). The solvent used for chromatographic separation will be removed and 2-(2-amino-1,6-dihydro-6-oxo9H-purin-9-yl)-methoxy-3-hydroxy-1-propanyl L-valinate salt will be isolated as a mixture of two diastereomers.

Isolation of Stereoisomers

From the Formula (I) it is apparent that the compound of the invention has one asymmetric carbon atom (chiral center) in the propanyl chain, in addition to the asymmetric carbon atom in L-valine. Therefore, two diastereomeric forms exist, the (R)- and (S)- form as determined by the rules of Cahn et al.

A number of methods suitable for the separation of the diastereomers can be used but the preferred methods use techniques that take advantage of the different physical properties of the two diastereomers. In general, the diastereomers are separated by chromatography but preferred are separation/resolution techniques depending on differences in solubility, such as fractional crystallization.

Specifics of the separation techniques applicable to the preparation of diastereomers of the Formula I are described in Jean Jacques, André Collet, Samuel H. Wilen, *Enantiomers, Racemates and Resolutions,* John Wiley & Sons, Inc. (1981), which is incorporated herein by reference.

Alternatively, the compound of the invention may be prepared using optically active reactants. When pure diastereomers of mono-L-valine ganciclovir are prepared the condensation step (d) is the preferred method of synthesis. However, if optically active reagents are being used it would be important to avoid the pH range above 6, as at the higher pH range interconversion of the free compound of Formula I occurs. For example, at pH 7 and 40° C. the diastereomeric mixtures of Formula I have a half-life of less than one hour.

The stereoconfiguration at the second chiral center of the compound of Formula I can be assigned by circular dichroism, preferably by Single Crystal X-Ray Analysis of a heavy atom derivative, or correlation with material prepared by total synthesis from a single glycerol enantiomer of known configuration.

The Manufacture of Crystalline 2-(2-Amino-1,6-dihydro-6-oxo-purin-9-yl)methoxy-3-hydroxy-1-propanyl-L-valinate The compound of the invention can be, and has been, produced in crystalline form. This is a decisive advantage over the compounds disclosed in the prior art which have been described as non-crystalline materials. The advantage resides in the fact that pharmaceutical formulations can be more easily produced with a crystalline material. A crystalline material can be processed efficiently and is susceptible of being more reproducibly characterized than a non-crystalline material, and the quality of the crystalline materials of the invention can be much more readily ascertained than that of non-crystalline materials.

In order to produce crystalline material it is preferred to use a salt of 2-(2-amino-1,6-dihydro-6-oxo-purin-9yl) methoxy-3-hydroxy-1-propanyl L-valinate. Preferred crystalline salts are the acetate and the hydrochloride salt. It is preferred to initiate crystallization of the salt by dissolving the hydrochloride or acetate salt in water and adding an organic solvent miscible with water such as methanol, ethanol, isopropanol, tetrahydrofuran or acetonitrile. Alternatively, the hydrochloride salt can be crystallized from an anhydrous lower alkanol solution, such as methanol, ethanol, by the addition of other organic solvents such as ethyl acetate, isopropanol, tetrahydrofuran or toluene.

The following preparations and examples are given to enable those skilled in the art to more clearly understand and to practice the present invention. They should not be considered as limiting the scope of the invention, but merely as being illustrative and representative thereof.

EXAMPLE 1

Preparation of (S)-2-(2-Amino-1,6-dihydro-6-oxo-purin-9-yl)methoxy-3-benzyloxy-propan-1-ol A. (R)-(1-Chloro-2-acetoxymethoxy-3-benzyloxy)propane HCl gas (dried by passing through concentrated $H_2SO_4$) was bubbled into a stirred mixture of (S)-(+)-benzyloxymethyloxirane (500 mg, 3.06 mmol) and paraformaldehyde (201 mg, 6.71 mmol) in dichloromethane (8 mL) at 0° C. until all the solid dissolved (ca. 45 min). The resulting solution was stored at 0° C. for 16 hours. After drying with magnesium sulfate, the solvent was evaporated to provide (R)-(1-chloro-2-chloromethoxy-3-benzyloxy) propane. This chloromethyl ether intermediate was dissolved in acetone (3 mL) and added dropwise to a mixture of potassium acetate (2.1 g, 21.4 mmol) in acetone (7 mL). The mixture was stirred at ambient temperature for 16 hours. The solid was filtered off and the filtrate concentrated. The residue was taken up in 20 mL of toluene and the washed with saturated sodium bicarbonate solution (10 mL) and water (2×20 mL). The organic layer was dried over sodium sulfate. After filtration, the filtrate was concentrated and the residue purified by flash chromatography over silica gel (hexane/ethyl acetate=7/1) to provide (R)-(1-chloro-2-acetoxymethoxy-3-benzyloxy)propane (810 mg, 2.97 mmol) as a colorless oil in 97% yield (the isomeric ratio was 12:1).

B. (R) 2-(2-Amino-1,6-dihydro-6-oxo-purin-9-yl)methoxy-1-chloro-3-benzyloxy-propane A solution of persilylated guanine (1.09 g, 2.95 mmol) in DMF (3.2 mL) was added to 81- mg of (R)-(1-chloro-2-acetoxymethoxy-3-benzyloxy)propane. The solution was stirred at 130° C. for 1 hour before trimethylsilyl trifluoromethanesulfonate was introduced. Stirring was continued at the same temperature for 4 hours. The mixture was cooled to room temperature and partitioned between water and ethyl acetate. The aqueous layer was extracted exhaustively with ethyl acetate. The combined organic layer was dried over magnesium sulfate, filtered and concentrated. The residue was purified by chromatography over silica gel to provide (R) 2-(2-amino-1,6-dihydro-6-oxo-purin-9-yl) methoxy-1-chloro-3-benzyloxy-propane along with its N-7 isomer. The ratio of N-9 to N-7 isomer was about 2.3:1.

C. (R)-2-(2-amino-1,6-dihydro-6-oxo-purin-9-yl)methoxy-1-acetoxy-3-benzyloxy-propane A mixture of the product from the previous step, potassium acetate, (large excess) and DMF was heated to reflux for 5 hours. The resulting brown mixture was cooled to room temperature and filtered through a plug of Celite. The filter bed was rinsed with methanol. The filtrate was evaporated and residual DMF removed in vacuo. The crude product was purified by flash chromatography over silica gel ($CH_2Cl_2$-methanol:10:1) to provide (R)-2-(2-amino-1,6-dihydro-6-oxo-purin-9-yl)methoxy-1-acetoxy-3-benzyloxy-propane as a pale yellow solid.

D. (S)-2-(2-Amino-1,6-dihydro-6-oxo-purin-9-yl)methoxy-1-benzyloxy-propan-3-ol

A mixture of (R)-2-(2-amino-1,6-dihydro-6-oxo-purin-9-yl)methoxy-1-acetoxy-3-benzyloxy-propane in 30% ammonia / methanol (1:2) was stirred at ambient temperature for 18 hours. The solvent was evaporated and the residue was triturated with a small amount of methanol. The pale yello solid was collected to give (S)-2-(2-Amino-1,6-dihydro-6-oxo-purin-9-yl)methoxy-1-benzyloxy-propan-3-ol. The mother liquor was concentrated and the residue recrystallized from hot methanol to give a second crop of the product.

EXAMPLE 2

Preparation of 2-(2-Amino-1,6-dihydro-6-oxo-purin-9-yl)methoxy-1-benyzloxy-propan-3-ol A. N2-Acetyl-2-(2-amino-1,6-dihydro-6-oxo-purin-9-yl) methoxy-1,3-bis(benzyloxy)propane, 54.2 g (114 mmol) was dissolved in refluxing ethanol (815 mL) and cyclohexane (610 mL) was added under a nitrogen atmosphere. A slurry of palladium hydroxide (16 g) in ethanol (50 mL) was added to the reaction mixture and the mixture was refluxed under nitrogen for 1.5 hrs. The hot mixture was filtered through Celite and the filtrate was concentrated on a rotary evaporator. The resulting crude reaction mixture was chromatographed on silica gel. Elution with 8% methanol/92% dichloromethane followed by 10% methanol/90% dichloromethane results in N2-acetyl-2-(2-amino-1,6-dihydro-6-oxo-purin-9-yl)methoxy-1,3-bis(benzyloxy)propane (starting material) (18.6 g, 16%) and N2-acetyl-2-(2-amino-1,6-dihydro-6-oxo-purin-9-yl)methoxy-1-benzyloxy-propan-3-ol, (17.6 g, 40%).

B. N2-Acetyl-2-(2-amino-1,6-dihydro-6-oxo-purin-9-yl) methoxy-1-benzyloxy-propan-3-ol, 21.9 g (56.5 mmol), was dissolved in methanol (200 mL) and ammonium hydroxide (101 mL) was added. The mixture was stirred over night at room temperature. Ethyl ether (400 mL) was added to the white slurry and the mixture was filtered. The precipitate was washed consecutively with ethyl ether (100 mL), water (100 mL) and ethyl ether (100 mL) and dried under high vacuum over night resulting in 15.9 g (46.13 mmol, 82%) of 2-(2-amino-1,6-dihydro-6-oxo-purin-9yl)methoxy-1-benzyloxy-propan-3-ol. Evaporation of the filtrate and suspension of the resulting precipitate in ethyl ether (200 mL) followed by filtration and drying under high vacuum results in an additional 2.3 g (6.7 mmol, 12%) of the product.

Analysis Calcd. for $C_{16}H_{19}N_5O_4$ (345.36): C, 55.65; H, 5.55; N, 20.28. Found: C, 55.25; H, 5.60; N, 20.12.

EXAMPLE 3

Preparation of 2-(2-Amino-1,6-dihydro-6-oxo-purin-9-yl)methoxy-3-hydroxy-1-propanyl-L-valinate A. 2-((2-Amino-1,6-dihydro-1,6-dihydro-6-oxo-purin-9-yl)methoxy)-3-benzyloxy-1-propanyl N-(benzyloxycarbonyl)-L-valinate N-Benzyloxycarbonyl-L-valine, 43.66 g (0.174 mol, 3 equivalents), was suspended in dichloromethane, 72 mL, and 1,3-dicyclohexylcarbodiimide, 14.34 g (69.5 mmol, 1.2 equivalents), was added. The mixture was stirred under nitrogen for 48 hrs. The mixture was filtered through a glass fritte and the white solid residue was washed with dichloromethane, 75 mL. The combined filtrate was stirred under nitrogen and a suspension of 2-(2-amino-1,6-dihydro-6-oxo-purin-9-yl)methoxy-3-benzyloxy-propan-1-ol, 20 g (57.91 mmol, 1 equivalents) in dimethylformamide, 90 mL, was added followed by 4-dimethylaminopyridine, 1.77 g (14.4 mmol, 0.25 equivalents). The mixture was stirred under nitrogen for 18 hours, poured into water 1200 mL, and extracted with a mixture of ethyl acetate (350 mL) and toluene (350 mL). The aqueous layer was separated and the organic layer was washed with half saturated sodium biocarbonate, 600 mL, followed by water (200 mL). The organic layer was dried over magnesium sulfate and concentrated under reduced pressure. The residue was precipated from a mixture of ethyl acetate and cyclohexane to give 2-((2-amino-1,6-dihydro-6-oxo-purin-9-yl)methoxy)-3-benzyloxy-1-propanyl N-(benzyloxycarbonyl)-L-valinate as an amorphous solid.

B. 2-(2-Amino-1,6-dihydro-6-oxo-purin-9-yl)methoxy-3-hydroxy-1-propanyl-L-valinate hydrochloride 2-(2-Amino-1,6-dihydro-6-oxo-purin-9-yl)methoxy)-3-benzyloxy-1-propanyl N-(benzyloxycarbonyl)-L-valinate, 224.8 g (0.39 mol), was dissolved in methanol, 1.2 L, and concentrated hydrocholoric acid, 32.4 mL (0.39 mol), was added dropwise. The mixture was placed under nitrogen and palladium on carbon, 67.4 g, was added. The mixture was hydrogenated in a Parr bomb under hydrogen (40 –100 psi, average 80 psi pressure) for 48 hours. 5 g additional palladium on carbon was added, and the mixture was hydrogenated at 100 psi for 24 hours. The mixture was filtered through a pad of Celite and the residue was washed with methanol, 1 L. The filtrate was evaporated to dryness under reduced pressure. The residue was dissolved in water, 150 mL, and heated to 60° C. Isopropanol (830 mL) was slowly added dropwise with stirring while maintaining the temperature (60–70°C.). The solution was slowly cooled to ambient temperature over 16 hours. The resulting crystalline solution was heated to 30° C. and additional isopropanol added, 220 mL. The mixture was allowed to slowly cool to a final temperature of −11° C. over 4 hours. The crystals were isolated by filtration and washed with 200 mL of cold 2% water/isopropanol to obtain 2-(2-amino-1,6-dihydro-6-oxo-purin-9-yl)methoxy-3-hydroxy-1-propanyl-L-valinate hydrochloride (120.5 g, 79% yield). The compound undergoes a phase change at 142° C. and decomposes at 175° C.

EXAMPLE 4

Preparation of Crystalline 2-(2-Amino-1,6-dihydro-6-oxo-purin-9-yl)methoxy-3-hydroxy-1-propanl-L-valinate Salt 2-(2-Amino-1,6-dihydro-6-oxo-purin-9-yl)methoxy-3-hydroxy-1-propanyl-L-valinate hydrochloride, 150 g, was dissolved in water, 150 mL, and heated to 50–60° C. Isopropanol (830 mL) was slowly added dropwise with stirring while slightly increasing the temperature to 60–70° C. The solution was slowly cooled to 25° C. over 20 hours. The resulting crystalline solution was heated to 30° C. and additional isopropanol added, 220 mL. The mixture was allowed to slowly cool to a final temperature of −11° C. over 6 hours. The crystals were isolated by filtration and washed with 200 mL of cold 2% water/isopropanol to obtain 2-(2-amino-1,6-dihydro-6-oxo-purin-9-yl)methoxy-3-hydroxy-1-propanyl-L-valinate hydrochloride crystals (135 g, 90% yield). The compound undergoes a phase change at 142° C. and decomposes at above 175° C.

In a similar manner 2-(2-amino-1,6-dihydro-6-oxo-purin-9-yl)methoxy-3-hydroxy-1-propanyl-L-valinate acetate may be prepared in crystalline form.

EXAMPLE 5

Preparation of (S)-2-(2-Amino-1,6-dihydro-6-oxo-purin-9yl)methoxy-3-hydroxy-1-propanyl-L-valinate hydrochloride A. (S)-2-(2-Amino-1,6-dihydro-6-oxo-purin-9-yl) methoxy)-3-benzyloxy-1-propanyl N-(benzyloxycarbonyl)-L-valinate N-Benzyloxycarbonyl-L-valinate, 437 mg (1.74 mmol; 3 equivalents), is suspended in dichloromethane, 1mL, and 1,3-dicyclohexylcarbodiimide, 143 mg (0.7 mmol, 1,2 equivalents), is added. The mixture is stirred under nitrogen for 48 hours. The mixture is filtered through a glass fritte and the white solid residue washed with dichloromethane, 1 mL. The combined filtrate is stirred under nitrogen and a suspension of (R)-2-(2-amino-1,6-dihydro-6-oxo-purin-9-yl)methoxy-3-benzyloxy-propan-1-ol, 200 mg (0.58 mmol, 1 equivalent) in dimethylformamide, 1.5 mL, is added followed by 4-dimethylaminopyridine, 18 mg (14.4 mmol, 0.25 equivalents). The mixture is stirred under nitrogen for 18 hours, poured into water, 12 mL, and extracted with a mixture of ethyl acetate (3.5 mL) and toluene (3.5 mL). The aqueous layer is separated and the organic layer washed with half saturated sodium bicarbonate, 6 mL, followed by water (2 mL). The organic layer is dried over magnesium sulfate and concentrated under reduced pressure. The residue is precipitated from a mixture of ethyl acetate and cyclohexane to give (S)-2-(2-amino-1,6-dihydro-6-oxo-purin-9-yl) methoxy)-3-benzyloxy-1-propanyl N-(benzyloxycarbonyl)-L-valinate as a solid.

B. (S)-2-(2-Amino-1,6-dihydro-6-oxo-purin-9-yl) methoxy-3-hydroxy-1-propanyl-L-valinate hydrochloride (S)-2-(2-Amino-1,6-oxo-purin-9-yl)methoxy)-3-benzyloxy- 1-propanyl N-(benzyloxycarbonyl)-L-valinate, 225 mg (3.9 mol), is dissolved in methanol, 12 mL, and concentrated hydrochloric acid, 0.3 mL (3.9 mmol), is added. The mixture is placed under nitrogen and palladium on carbon, 674 mg, is added. The mixture is hydrogenated in a Parr bomb under hydrogen (40–100 psi, average 80 psi pressure) for 48 hours. 50 mg additional palladium on carbon are added, and the mixture hydrogenated at 100 psi for 24 hours. The mixture is filtered through a pad of Celite and the residue is washed with methanol, 10 mL. The filtrate is evaporated to dryness under reduced pressure. The residue is dissolved in water 1.5 mL, and heated to 60° C. Isopropanol (8 mL) is slowly added with stirring while maintaining the temperature (60–70° C.). The solution is slowly cooled to ambient temperature over 16 hours. The resulting solution is heated to 30° C. and additional isopropanol added, 2 mL. The mixture is allowed to slowly cool to a final temperature of −11° C. over 4 hours. The crystals are isolated by filtration and washed with 2 mL of cold 2% water/isopropanol to obtain (S)-2-(2-amino-1,6-dihydro-6-oxo-purin-9yl) methoxy-3-hydroxy-1-propanyl-L-valinate hydrochloride.

EXAMPLE 6

Preparation of 2-(2-Amino-1,6-dihydro-6-oxo-purin-9-yl)methoxy-3-hydroxy-1-propanyl-L-valinate acetate from 2-(2-Amino-1,6-dihydro-6-oxo-purin-9-yl)methoxy-1,3-propanediyl bis (L-valinate) bis acetate 2-((2-Amino-1,6-dihydro-6-oxo-9H-purin-9-yl)methoxy)-1,3-propanediyl bis-L-valinate bis acetic acid salt, 100 mg (lyophilized sample contained 0.6 equivalents of excess acetic acid, 0.164 mmol (=a total of 0.426 mmol of acetic acid) was dissolved in de-ionized water, 0.4 mL, and partially neutralized by the addition of 24 mL of a 0.015M ammonium hydroxide solution (=0.36 mmol). The mixture was left at room temperature for 67 hrs. The sample was injected in two equal lots onto a preparative reverse phase HPLC column (YMC-Pack, ODS-AM DM-33.5, 2×250 mm; YMC Inc.). Separation was achieved with a solvent system of 10% methanol /90% 0.1M ammonium acetate buffered to pH 4 with acetic acid, flow rate: 9.5 mL/min and the detector set to 256 nm. The two peaks representing the two diastereomers of the mono ester product were collected. The solvent was removed under high vacuum to about 2 mL and the residue was lyophilized twice from water containing acetic acid (0.1%) to remove the buffer. 45 mg (0.112 mmol=68%) of 2-((2-amino-1,6-dihydro-6-oxo-9H-purin-9-yl)ethoxy)-3-hydroxy-1-propanyl L-valinate acetic acid salt was isolated as a mixture of two diastereomers with the following characteristic peaks of the NMR spectrum: $^1$H NMR (300 Mhz) DMSO-$d_6$ solution: δ 7.78 (1 H, s, H C-8), 6.48 and 6.45 (2 br.s., 2 H, $NH_2$), 5.44 (mAB, J=11 Hz) and 5.43 (s) total of 2 H, CH2; 1.91 (s, 3 H, $CH_3COO^-$), 0.83+0.82 (2 d, J=7 Hz, 3 H, $CH_3$), 0.75+0.76 (2 d, J=7 Hz, 3 H, $CH_3$).

EXAMPLE 7

Separation of (R,S) 2-(2-amino-1,6-dihydro-6-oxo-purin-9-yl)methoxy-3-hydroxy-1-propanyl-L-valinate A solution of (R,S) 2-(2-amino-1,6-dihydro-6-oxo-purin-9-yl)methoxy-3-hydroxy-1-propanyl-L-valinate (1.66 g) in 90% 0.1M ammonium acetate, acidified to pH 4 with acetic acid, 10% methanol (9.6 mL) was applied to a YMC-Pack ODS-AM HPLC column (cat. no. DM-33-5; size, 250×20 mmI.D.; particle, S-5 mm, 120 A) in 48 injections of 200 μL with elution at 9.5 mL/min. using a mobile phase of 90% 0.1M ammonium acetate acidified to pH 4 with acetic acid, 10% methanol. The peaks were detected using Knauer Variable Wavelength Monitor set to 256 nm and the fractions collected manually. Three sets of fractions were collected, peak 1 (retention time 24.4 min.), an overlapping region between the peaks and peak 2 (retention time 27.8 min.). The fractions of each set were combined, evaporated under reduced pressure to remove the methanol then lyophilized to remove the remaining volatile components. The residue was dissolved in water, acidified to pH 4 with acetic acid and lyophilized again yielding peak 1 (1.57 g) and peak 2 (0.91 g). HPLC analysis of the products using a YMC-Pack ODS-AM Column (cat. no. RM-33-5; size, 250×4.6 mmI.D.; particle, S-5 mm, 120 A) with elution at 0.5 mL/min. using a mobile phase of 90% 0.1M ammonium acetate, acidified to pH 4 with acetic acid, 10% methanol indicated that peak 1 (retention time 24.4 min. on the preparative column) contained a mixture 70% peak 1 (retention time 21.1 min.). 26.4% peak 2 (retention time 24.6 min.) and 2.8% fully hydrolyzed product (retention time 12.4 min.); and peak 3 (retention time 27.8 min. on the preparative column) contained a mixture 68.5% peak 2 (retention time 22.0 min.), 27.5% peak 1 (retention time 20.2 min.) and 4% fully hydrolyzed product (retention time 11.6 min.). Peak 2 (0.91 g) and peak 1 (1.57 g) were each dissolved in 90% 0.1M ammonium acetate acidified to pH 4 with acetic acid, 10% methanol (3.60 mL) and purified again using the system outlined before in of 18 injections of 200 mL. Two sets of fractions corresponding to peaks 1 and 2 were collected, combined, partially evaporated under reduced pressure to remove the methanol and the remainder lyophilized to remove the remaining volatile components. The residue from each set of fractions was dissolved in water, carefully acidified to pH 4 with acetic acid and lyophilized once more. The fractions corresponding to peak 1 yielded a white fluffy solid (0.70 g) which appeared hygroscopic on exposure to air; HPLC analysis (performed as outlined before) indicated this to be a mixture containing 94.9% peak 1 (retention time 21.1 min.) 4.6% peak 2 (retention time 26.7 min.) and 0.5% fully hydrolyzed product (retention time 11.8 min.); $^1$H NMR analysis ($^{66}$DMSO, δ values quoted relative to tetramethylsilane as internal standard) showed characteristic peaks δ 5.43 ($m_{AB}$, 2 H, $J_{AB}$=11.1 Hz, $d_A$ 5.44, $d_B$ 5.43), 3.02 (d, 1 H, J=5.2 Hz), 0.82 (d, 3 H, J=6.8 Hz), 0.75 (d, 3 H, J=6.8 Hz). The fractions corresponding to peak 2 yielded a white fluffy solid (0.81 g) which appeared hygroscopic on exposure to air; HPLC analysis (performed as outlined before) indicated this to be a mixture containing 91.0% peak 2 (retention time 29.8 min.) 8.4% peak 1 (retention time 28.4 min.) and 0.6% fully hydrolyzed product (retention time 14.4 min.); $^1$H NMR analysis ($^{66}$DMSO, δ values quoted relative to tetramethylsilane as internal standard) showed characteristic peaks d 5.43 (s, 2 H), 2.99 (d, 1 H, J=5.2 Hz), 0.83 (d, 3 H, J=6.8 Hz), 0.76 (d, 3 H, J=6.8 Hz).

EXAMPLE 8

A. Preparation of (R) 2-(2-amino-1,6-dihydro-6-oxo-purin-9-yl)methoxy-3-benzyloxy-1-propanyl (N-benzyloxycarbonyl)-L-valinate To a solution of N-benzyloxycarbonyl-L-valine (327 mg, 1.30 mmol, 3 equivalents) in dichloromethane (25 mL) under nitrogen was added 1,3-dicyclo-hexylcarbodiimide (134 mg, 0.65 mmol, 1.5 equivalents) and the reaction mixture stirred at room temperature for 13.5 hours. The resulting mixture was filtered to remove the insoluble material and the solvent evaporated under reduced pressure using a rotary evaporator. The resulting white foam was dissolved in dry DMF (10 mL) added directly to a solution of (S)-2-(2-amino-1,6-dihydro-6-oxo-purin-9-yl)methoxy-3-benzyloxy-1-propan-1-ol (150 mg, 0.43 mmol, 1 equivalent) also in dry DMF (10 mL). 4.4-Dimethylamino-pyridine (13 mg, 0.11 mmol, 0.25 equivalents) was added to the DMF solution and the reaction mixture left to stir at room temperature for 27 hours at which point TLC analysis indicated consumption of the starting materials. The reaction mixture was evaporated under reduced pressure and the crude product purified by flash chromatography using a mobile phase of 95% methylene chloride, 5% methanol to yield the title compound as an amorphous solid (158 mg, 63%).

B. Preparation of (R)-2-(2-amino-1,6-dihydro-6-oxo-purin-9-yl)methoxy-3-hydroxy-1-propanyl-L-valinate hydrochloride (R)-2-(2-amino-1,6-dihydro-6-oxo-purin-9-yl)methoxy-3-benzyloxy-1-propanyl (N-benzyloxy-carbonyl)-L-valinate (158 mg, 0.27 mmol) was dissolved in methanol (15 mL) and concentrated hydrochloric acid (24 mL, 0.27 mmol) added. The mixture was placed under nitrogen and 10% palladium on carbon (48 mg) was added. The mixture was hydrogenated in a Parr shaker under hydrogen (50 psi of pressure) for 5 hours. The mixture was filtered through a pad of Celite and the residue washed with methanol (25 mL). Evaporation of the combined filtrate and washings under reduced pressure yielded the title compound (107 mg, 95%). HPLC analysis of the product using a YMC-Pack ODS-AM column (cat. no. RM-33-5; size, 250×4.6 mmI.D.; particle, S-5 mm, 120 A) with elution at 0.5 mL/min. using a mobile phase of 90% 0.1M ammonium acetate acidified to pH 4 with acetic acid, 10% methanol indicated it to be a 85:15 mixture of (R) and (S) diastereomers.

EXAMPLE 9

Determination of Oral Absorption (Bioavailability) in the Rat

The following assay was used to determine the oral absorption (oral bioavailability) of the compound of Formula I (L-monovaline ester of ganciclovir) and of other ganciclovir amino acid esters, other ganciclovir esters and ethers examined for comparative purposes.

To measure the oral bioavailability of a compound first the plasma level of the compound in male rats was determined after a single oral (p.o.) dose of the compound. To measure the oral bioavailability of a pro-drug, first the plasma level of the active compound, in this case ganciclovir, was determined in male rats after a single po dose of the pro-drug. Then the plasma level of the active compound, ganciclovir, is determined in male rats after a single intravenous (iv) dose of the compound. For ganciclovir the single dose in each case, po and iv, is 10 mg/kg; for a prodrug ester (including the L-monovaline ester of ganciclovir) the single dose in each case, oral and iv, is a dose equimolar to 10 mg/kg of ganciclovir. From the two measurements following p.o. and iv administration, the oral bioavalability of a compound was calculated by dividing the total area under the concentration vs. time curve following p.o. administration by the total area under the concentration vs. time curve following iv administration, appropriately corrected for dose, according to the equation:

$$F_{(p.o.)}(\%) = [AUC_{(p.o.)}/AUC_{(i.v.)}] \times [Dose_{(i.v.)}/Dose_{(p.o.)}] \times 100$$

The AUC (total area under the curve) values were calculated over the entire time range which was analyzed from 0–24 hr.

The dose vehicle for oral and intravenous dosing consisted normal saline containing 2% acetic acid. In both cases the compound concentration was equivalent to 4.0 mg/mL ganciclovir with a dose rate equivalent to 10 mg/kg (2.5 mL/kg) of ganciclovir. A 200 gm rat received 0.5 mL of the oral drug solution by gavage or via injection into the tail vein.

The rats were acclimatized to the laboratory environment for three days and fasted overnight before start of the experiment and until 4 hours after dosing. Blood was collected from 4 rats at each of the following times: 0 min (pre-dose), 5 min (iv only), 15 min, 30 min, 1 hr, 2 hr, 3 hr, 5 hr, 7 hr 10 hr and 24 hr. The blood was immediately centrifuged to obtain the plasma and the plasma frozen at −20 ° C. until analysis.

Assay of Ganciclovir in Plasma

Aliquots of plasma (0.50 mL) were mixed with 0.020 mL of internal standard (acyclovir 15 $\mu$g/mL in 10% methanol/water) and 3.0 mL of acetonitrile. The mixture was vortexed and the resulting precipitate was removed by centrifugation (4,000 g, 10 min). The supernatant was evaporated to dryness under nitrogen and reconstituted in 200 $\mu$L of HPLC mobile phase. Aliquots (0.05 mL) were analyzed by HPLC using a Keystone Hypersil BDS, 250×4.6 mm C 18 column. The mobile phase contained 2% acetonitrile in 30 mM sodium phosphate buffer containing 5 mM heptane sulfonic acid, pH 2.0 and was pumped at 1.0 mL/min. Ganciclovir and internal standard were detected and measured by UV absorbance at 254 nm.

| COMPOUND | ORAL BIO-AVAILABILITY (F %) | REFERENCE |
|---|---|---|
| Ganciclovir (G) {2-(2-Amino-1,6-dihydro-6-oxo-purin-9-yl)-methoxy-1,3-propanediol} | 7.9 | US 4,355,032 |
| G-bis(propionic acid) ester | 17.7 | J. Pharm Sci. 76, p. 180–184 (1987) |
| G-bis (L-valine) ester | 52.0 | EP 0 375 329 |
| G-L-valine ester benzyl ether | non-detectable | — |
| G-bis(phenylglycine) ester diacetate | 8.18 | |
| G-dibenzyl ether | non-detectable | |
| Amino Acid Ester of the Invention | | |
| G-L-valinate acetate | 84.0 | |
| G-L-valinate hydrochloride | 98.1 | |

ORAL BIOAVAILABILITY

EXAMPLE 10

Determination of Oral Absorption (Bioavailability) in the Cynomolgus Monkey

The following assay was used to determine the oral absorption (oral bioavailability) of the compound of Formula I in the Cynomolgus Monkey.

Animals, Dosing and Sample Collection

Male cynomolgus monkeys weighing 5 to 7 kilos were used. The animals were fed monkey chow, fruit and water and maintained on a 12 hour light cycle. The tested compounds were formulated at a concentration equimolar to a 10 mg/mL solution of ganciclovir in saline. The oral formulation was administered by gavage at a rate of 1.0 mL/kg for a final dose equimolar to a 10 mg/kg dose of ganciclovir. The iv formulation of ganciclovir was formulated in saline containing 0.2% HCl at a concentration of 20 mg/mL and administered at a rate of 0.5 mL/kg.

The animals were fasted beginning the evening prior to dosing and until 4 hr after dosing. Blood samples were taken from each monkey at 0 (predose), 5 min (iv only), 15 min, 30 min, 1 hr, 2 hr, 3 hr, 5 hr, 7 hr, 10 hr and 24 hr after dosing. The blood samples were collected in heparinized syringes and the plasma was immediately isolated by centrifugation and frozen at −20° C. until analysis.

Assay of Ganciclovir in Plasma

Aliquots of plasma (0.50 mL) were mixed with 0.020 mL of internal standard (acyclovir, 15 µg/mL in 10% methanol/water) and 3.0 mL of acetonitrile. The mixture was vortexed and the resulting precipitate was removed by centrifugation (4,000 g, 10 min). The supernatant was evaporated to dryness under nitrogen and reconstituted in 200 µL of HPLC mobile phase. Aliquots (0.05 mL) were analyzed by HPLC using a Keystone Hypersil BDS, 250×4.6 mm C 18 column. The mobile phase contained 2% acetonitrile in 30 mM sodium phosphate buffer containing 5 mM heptane sulfonic acid, pH 2.0 and was pumped at 1.0 mL/min. Ganciclovir and internal standard were detected and measured by UV absorbance at 254 nm.

The bioavailability (F) is calculated according to the equation given in Example 9.

The prodrug 2-(2-amino-1,6-dihydro-6-oxo-purin-9-yl)methoxy-3-hydroxy-1-propanyl-L-valinate had an oral bioavailability of 35.7%. 2-(2-Amino-6-dihydro-6-oxo-purin-9-yl)methoxy-1,3-propanediyl bis (L-valinate) had an oral bioavailability of 23.5%. Ganciclovir has a bioavailability of 9.9%. Giving the same prodrug orally and ganciclovir iv to the same monkeys results in a mean oral bioavailability for the prodrug of 41.6%.

EXAMPLE 11

The following examples of the proposed ganciclovir L-valine monoester capsules contain as excipients povidone, a binder; corn starch, a disintegrant; and stearic acid, a lubricant and glidant; which are filled into a two piece hard gelatin capsule shell. Water is the granulating liquid, and is essentially removed during processing.

Quantitative Composition of Ganciclovir L-Valine Monoester Capsules
(One Capsule Three Times Per Day)

| Ingredients | Weight Per Capsule (mg) | % W/W |
| --- | --- | --- |
| Ganciclovir L-valine monoester hydrochloride | 390.00 | 92.75 |
| Povidone | 12.61 | 3.00 |
| Corn starch | 16.81 | 4.00 |
| Stearic acid[1] | 1.05 | 0.25 |
| Water[2] | | |
| Total fill weight (theoretical)[3] | 420.47 | 100.00 |

The powder blend is filled into two piece hard gelatin capsule shells.

[1]The amount of stearic acid may vary from 0.1% to 5.0% of the weight.
[2]The amount of water may vary to produce an acceptable granulation, and is dried off.
[3]The total fill weight (theoretical) does not include the residual moisture that will be present in the finished product.

Quantitative Composition of Ganciclovir L-Valine Monoester Capsules
(Two Capsules Three Times Per Day)

| Ingredients | Weight Per Capsule (mg) | % W/W |
| --- | --- | --- |
| Ganciclovir L-valine monoester hydrochloride | 312.00 | 92.75 |
| Povidone | 10.09 | 3.00 |
| Corn Starch | 13.45 | 4.00 |
| Stearic Acid | 0.84 | 0.25 |
| Water[2] | | |
| Total fill weight (theoretical)[3] | 336.38 | 100.00 |

[1]The amount of stearic acid may vary from 0.1% to 5.0% of the weight.
[2]The amount of water may vary to produce an acceptable granulation, and is dried off.
[3]The total fill weight (theoretical) does not include the residual moisture that will be present in the finished product.

The powder blend is filled into two piece hard gelatin capsule shells.

Example of the Manufacturing Procedure for Ganciclovir L-Valine Monoester Capsules 1. Blend the ganciclovir L-valine monoester and part of the corn starch in a suitable manner.
2. Dissolve the povidone in the water with stirring.
3. Add (2) to (1) while continuing to mix to form a granulation.
4. Mill the wet granulation if necessary.
5. Dry the wet granulation in a dryer.
6. Pass the dry granulation, the remaining corn starch, and the stearic acid through a mill.
7. Blend (6) in a suitable mixer.
8. Encapsulate the appropriate amount of (7) into 2 piece hard gelatin capsule shells.

What is claimed is:

1. The compound 2-(2-amino-1,6-dihydro-6-oxo-purin-9-yl)methoxy-3-hydroxy-1-propanyl-L-valinate hydrochloride in crystalline form.

2. An antiviral pharmaceutical composition comprising the compound of claim 1 and a pharmaceutically acceptable excipient.

3. A method of treating an animal infected with a virus selected from herpes simplex virus and cytomegalovirus, comprising administering a therapeutically effective amount of the compound of claim 1 to the animal.

4. The method of claim 2 where the compound is administered orally.

5. The method of claim 3 where the herpes viral infection is a cytomegalovirus infection.

6. The method of claim 5 wherein the compound is administered orally.

* * * * *

UNITED STATES PATENT AND TRADEMARK OFFICE
CERTIFICATE OF CORRECTION

PATENT NO. : 6,083,953 Page 1 of 1
APPLICATION NO. : 08/812991
DATED : July 4, 2000
INVENTOR(S) : John Joseph Nestor et al.

It is certified that error appears in the above-identified patent and that said Letters Patent is hereby corrected as shown below:

Title Page, item (75)
Inventors should read:

Inventors: John Joseph Nestor, Cupertino; Scott William Womble, Fremont; Hans Maag, Menlo Park; Charles A. Dvorak, Palo Alto; Paul A. Fatheree, San Francisco, all of California.

Signed and Sealed this

Twenty-fourth Day of July, 2007

JON W. DUDAS
*Director of the United States Patent and Trademark Office*